(12) United States Patent
de la Rama et al.

(10) Patent No.: US 8,620,400 B2
(45) Date of Patent: *Dec. 31, 2013

(54) DUAL-DEFLECTING ELECTROPHYSIOLOGY CATHETER

(71) Applicant: St. Jude Medical, Atrial Fibrillation Division, Inc., St. Paul, MN (US)

(72) Inventors: Alan de la Rama, Cerritos, CA (US); Phuong-Oahn Phung, Fountain Valley, CA (US); Pianka Roy, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/757,947

(22) Filed: Feb. 4, 2013

(65) Prior Publication Data

US 2013/0144208 A1 Jun. 6, 2013

Related U.S. Application Data

(63) Continuation of application No. 12/760,337, filed on Apr. 14, 2010, now Pat. No. 8,369,923.

(51) Int. Cl.
*A61B 5/042* (2006.01)
(52) U.S. Cl.
USPC .......................................... 600/374; 600/381
(58) Field of Classification Search
USPC ................................... 600/374, 381; 606/41
See application file for complete search history.

(56) References Cited

U.S. PATENT DOCUMENTS

| | | | | |
|---|---|---|---|---|
| 5,383,852 | A | * | 1/1995 | Stevens-Wright ......... 604/95.04 |
| 5,552,713 | A | * | 9/1996 | Rashidi ......................... 324/555 |
| 5,861,024 | A | * | 1/1999 | Rashidi ......................... 607/122 |
| 6,572,611 | B1 | * | 6/2003 | Falwell ............................ 606/41 |
| 6,671,533 | B2 | * | 12/2003 | Chen et al. ..................... 600/374 |
| 7,013,169 | B2 | * | 3/2006 | Bowe ............................. 600/374 |
| 7,245,955 | B2 | | 7/2007 | Rashidi |
| 7,606,609 | B2 | | 10/2009 | Muranushi et al. |
| 8,369,923 | B2 | * | 2/2013 | de la Rama et al. .......... 600/374 |
| 2002/0065514 | A1 | * | 5/2002 | Rashidi ............................ 606/41 |
| 2003/0109778 | A1 | * | 6/2003 | Rashidi ......................... 600/374 |
| 2003/0208198 | A1 | * | 11/2003 | Hayzelden et al. ............. 606/41 |
| 2007/0038056 | A1 | | 2/2007 | Pappone et al. |

* cited by examiner

*Primary Examiner* — Lee S Cohen
(74) *Attorney, Agent, or Firm* — Wiley Rein LLP

(57) ABSTRACT

An electrophysiology catheter includes a tubular body having a proximal region, a neck region, and a distal region predisposed into a loop and including electrodes. A first deflection wire extends through at least a portion of the proximal region of the catheter body and includes a first flattened section, while a second deflection wire extends through the neck region and at least a portion of the distal region and includes a second flattened section within the neck region. A first activation wire is joined to the flattened section of the first deflection wire, while a second activation wire is joined to the flattened section of the second deflection wire. Thus, forces acting on the first and second activation wires, such as forces imposed by a handle-based actuator, are respectively transmitted to the first and second deflection wires, thereby deflecting the proximal and neck regions, respectively.

20 Claims, 8 Drawing Sheets

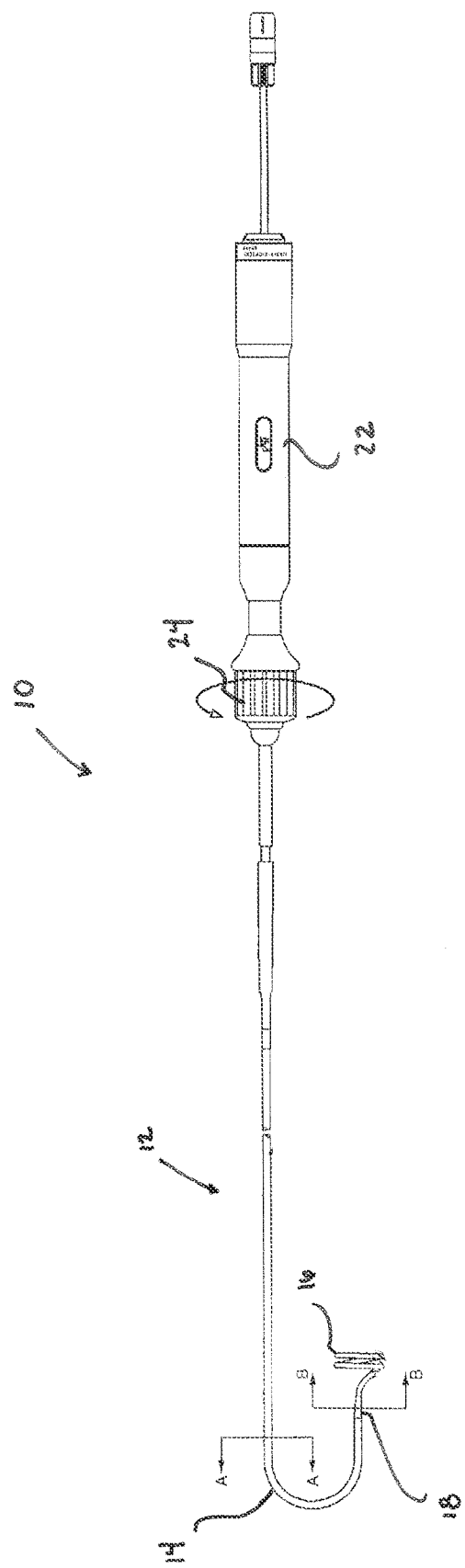

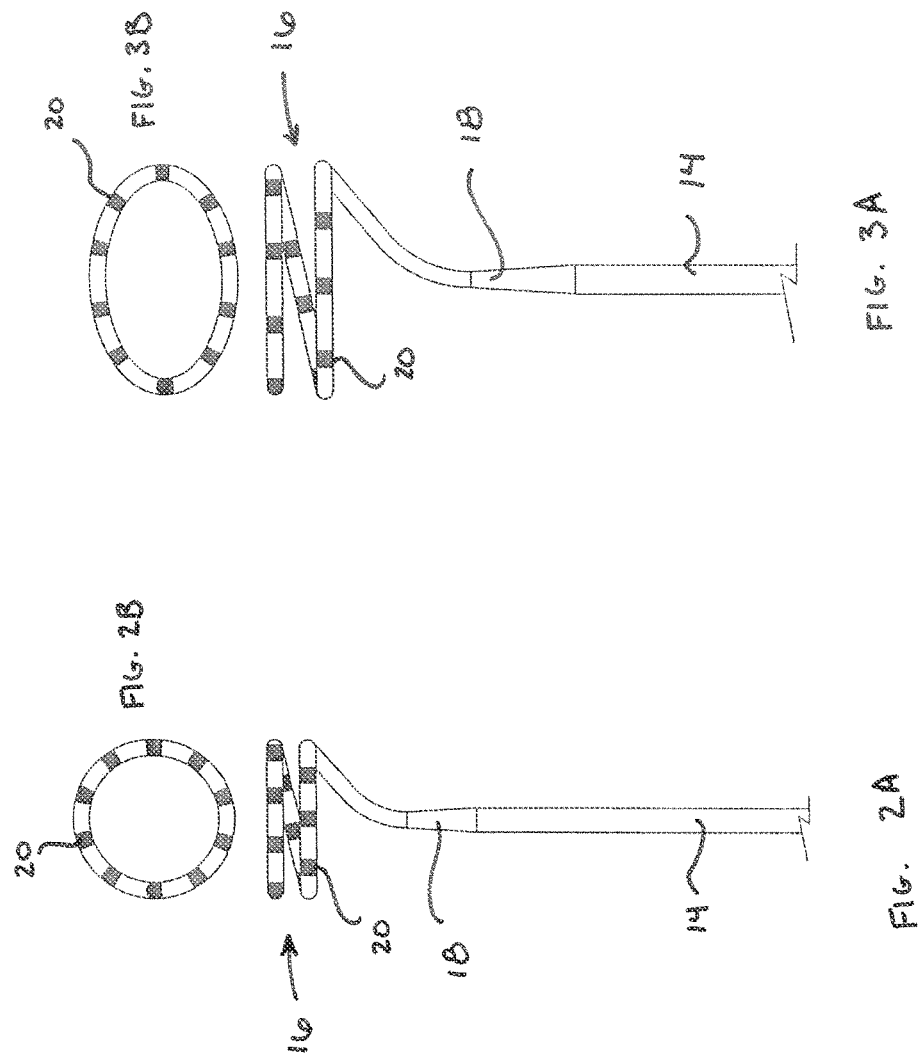

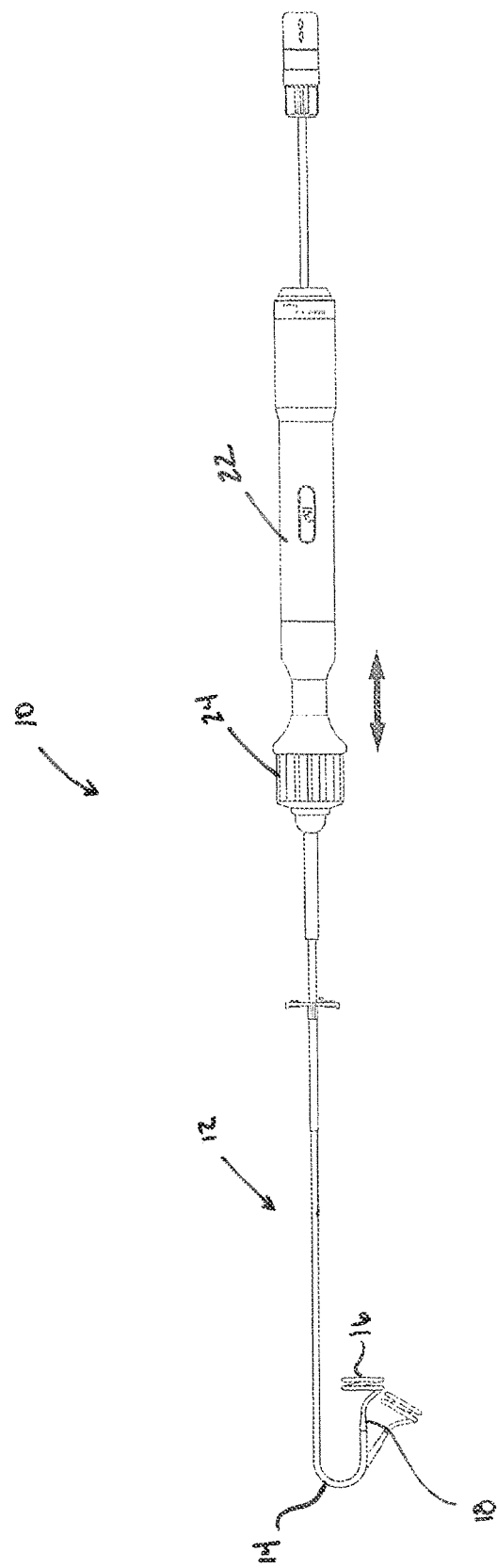

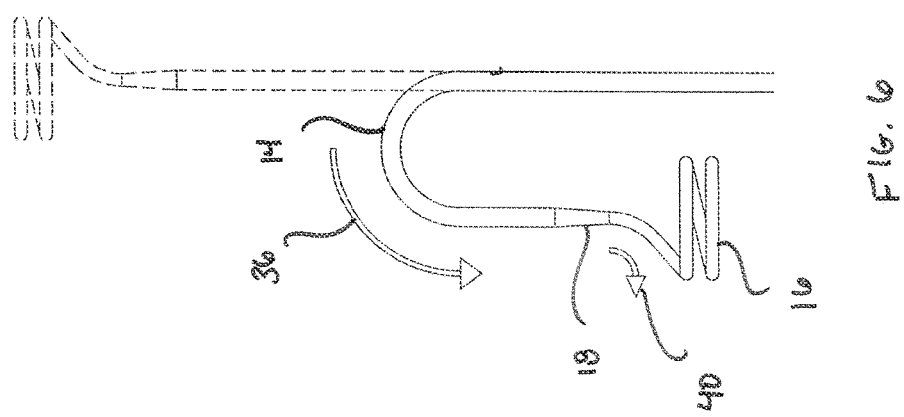

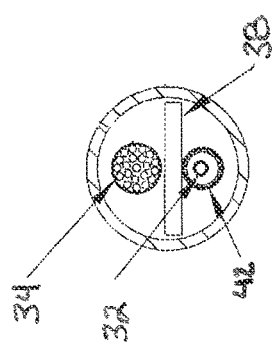

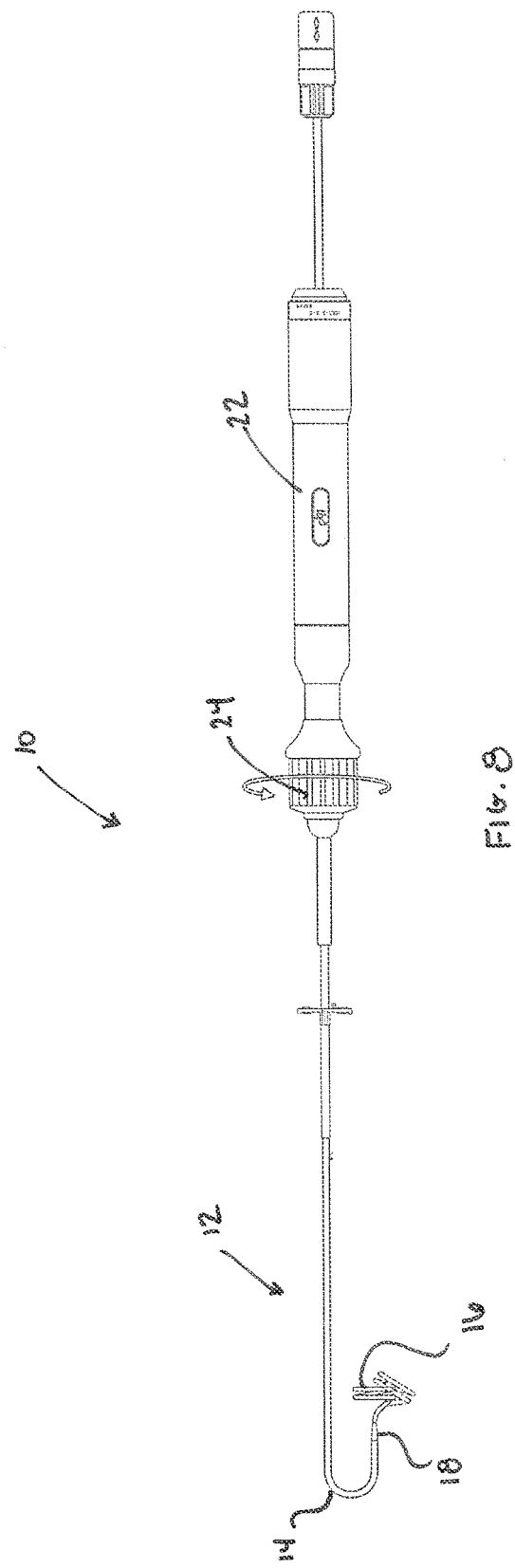

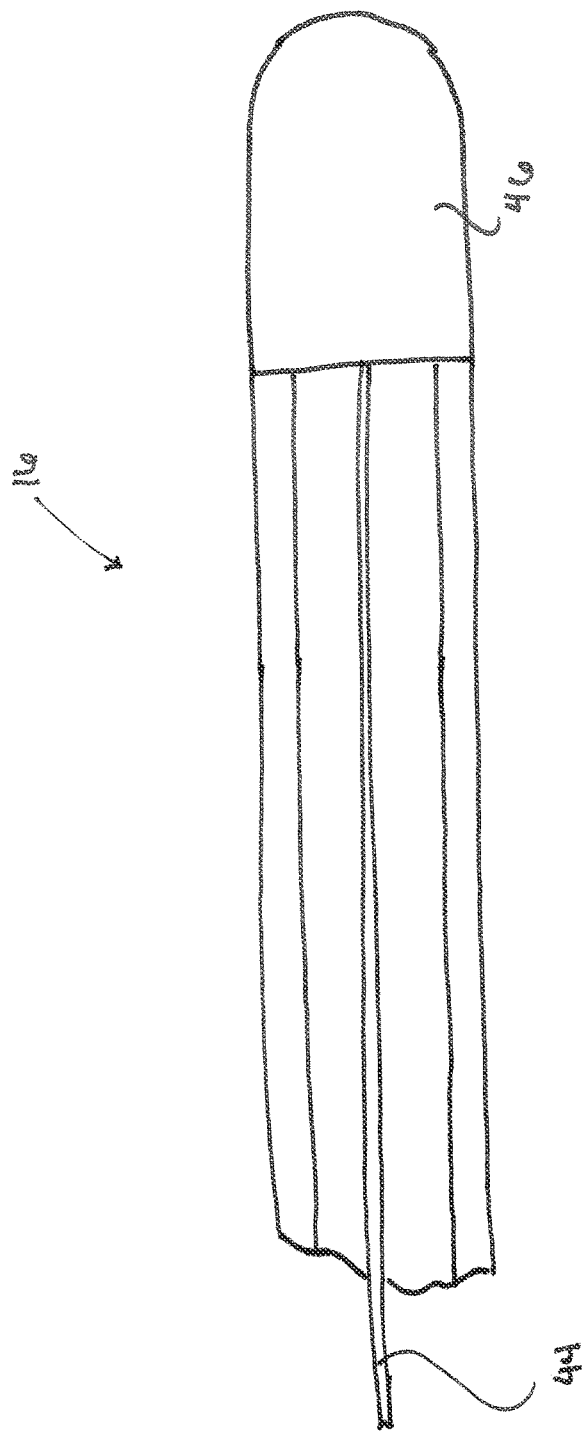

DUAL-DEFLECTING ELECTROPHYSIOLOGY CATHETER

CROSS-REFERENCE TO RELATED APPLICATIONS

This application is a continuation of U.S. application Ser. No. 12/760,337, filed 14 Apr. 2010 (the '337 application), now U.S. Pat. No. 8,369,923 (issued 5 Feb. 2013), which is hereby incorporated by reference as though fully set forth herein.

BACKGROUND OF THE INVENTION a. Field of the Invention

The instant invention relates to catheters for use in medical procedures. In particular, the instant invention relates to an electrophysiology catheter for use in diagnostic and therapeutic procedures at or near an annular region of a patient's anatomy, such as the ostium of a pulmonary vein.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical electrophysiology catheter includes an elongate shaft and one or more electrodes on the distal end of the shaft. The electrodes may be used for ablation, diagnosis, or the like. Oftentimes, these electrodes are ring electrodes that extend about the entire circumference of the catheter shaft.

One specific use of an electrophysiology catheter is to map the atrial regions of the heart, and in particular the pulmonary veins, which are often origination points or foci of atrial fibrillation. Such electrophysiology mapping catheters typically have at least a partial loop shape at their distal end in order to surround the pulmonary vein ostia. Because of varying patient anatomies, however, it may be challenging to properly place the looped section of the catheter precisely in the pulmonary vein ostia.

BRIEF SUMMARY OF THE INVENTION

Accordingly, it is an object of the present invention to provide an electrophysiology catheter having an enhanced ability to customize the shape of the catheter for a particular patient's individual anatomy.

Another object of the present invention is to provide an electrophysiology catheter that allows the looped portion to deflect relative to the remainder of the catheter body, thereby permitting the angle of the loop to be "fine tuned."

According to a first aspect, the present invention provides an electrophysiology catheter including: a tubular catheter body having a proximal region, a neck region, and a distal region predisposed into at least a partial loop; a plurality of electrodes disposed on the distal region; a handle joined to the proximal region; a first deflection wire extending through at least a portion of the proximal region of the catheter body and including a first flattened section; a second deflection wire extending through the neck region and at least a portion of the distal region and including a second flattened section within the neck region; a first activation wire extending from the handle and joined to the first flattened section of the first deflection wire such that forces acting on the first activation wire are transmitted to the first deflection wire in order to deflect the proximal region of the tubular catheter body; and a second activation wire extending from the handle and joined to the second flattened section of the second deflection wire such that forces acting on the second activation wire are transmitted to the second deflection wire in order to deflect the neck region of the tubular catheter body. Optionally, the second deflection wire may be a shape memory material, such as nickel titanium. The second deflection wire may also be configured to include a cylindrical section extending distally from the second flattened section through at least a portion of the distal region. In other embodiments of the invention, a spring coil is provided that surrounds at least a portion of the second activation wire.

Typically, the handle of the electrophysiology catheter will also include a first actuator operably coupled to the first activation wire and a second actuator operably coupled to the second activation wire. In some embodiments of the invention, it is contemplated that the electrophysiology catheter will include a third activation wire adapted to alter a radius of curvature of the at least a partial loop. Likewise, the handle of the electrophysiology catheter may include a third actuator operably coupled to the third activation wire.

Also disclosed herein is an electrophysiology catheter including: an elongate catheter body including a proximal region, a distal region, and a neck region joining the distal region to the proximal region; a plurality of electrodes disposed on the distal region; a first deflection mechanism including a first flat wire disposed within the proximal region of the catheter body and operable to deflect the proximal region of the catheter body; a shape memory structure extending through at least a portion of the distal region and shaping the portion of the distal region into at least a partial loop; and a second deflection mechanism including a second flat wire disposed within the neck region of the catheter body and operable to deflect the neck region of the catheter body, wherein a distal end of the second flat wire is coupled to a proximal end of the shape memory structure. Optionally, the shape memory structure may be operable to alter a radius of curvature of the at least a partial curve of the distal region.

It is contemplated that the first deflection mechanism and the second deflection mechanism respectively may deflect the proximal region and the neck region of the catheter body in the same plane. Alternatively, the first deflection mechanism and the second deflection mechanism respectively may deflect the proximal region and the neck region of the catheter body in different planes. In general, the first deflection mechanism includes a first activation wire coupled to the first flat wire such that forces acting on the first activation wire are transferred to the first flat wire, while the second deflection mechanism includes a second activation wire coupled to the second flat wire such that forces acting on the second activation wire are transferred to the second flat wire. In turn, a handle coupled to the proximal region of the catheter body includes a first actuation mechanism operably coupled to the first activation wire and a second actuation mechanism operably coupled to the second activation wire.

In yet another aspect, the present invention provides a method of performing an electrophysiology procedure. The method generally includes the steps of: providing an electrophysiology catheter including a proximal region, a neck region, a distal region disposed into at least a partial loop, a plurality of electrodes disposed on the distal region, a first deflection mechanism including a first flat wire operable to deflect the proximal region of the electrophysiology catheter, and a second deflection mechanism including a second flat wire operable to deflect the neck region of the electrophysiology catheter; introducing the electrophysiology catheter into a patient's body proximate an ostium of interest; actuating the first deflection mechanism to deflect the proximal region of the catheter in order to orient the distal region generally towards the ostium of interest; and actuating the second deflection mechanism to deflect the neck region of the catheter in order to refine a position of the distal region relative to the ostium of interest. The electrophysiology catheter may also include a radius of curvature actuation mechanism that is operable to alter a radius of curvature of the at least a partial loop, such that the method may also include a step of actuating the radius of curvature actuation mechanism to adjust the radius of curvature of the at least a partial loop to conform to a shape of the ostium of interest.

An advantage of an electrophysiology catheter according to the present invention is that the distal region thereof, including the loop used in electrophysiological procedures at or near an annular region, can be deflected relative to the remainder of the catheter body.

Another advantage of an electrophysiology catheter according to the present invention is that its shape can be tailored to a particular patient's individual anatomy.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a side view of an exemplary electrophysiology catheter.

FIG. 2A is a close up of a portion of an electrophysiology catheter according to some embodiments of the present invention.

FIG. 2B is an end view of the electrophysiology catheter of FIG. 2A.

FIG. 3A is a close up of a portion of an electrophysiology catheter according to additional embodiments of the present invention.

FIG. 3B is an end view of the electrophysiology catheter of FIG. 3A.

FIG. 5 depicts the deflection of the proximal region of the electrophysiology catheter of FIG. 1.

FIG. 6 depicts the deflection of both the proximal region and the neck region of the electrophysiology catheter of FIG. 1.

FIG. 7 is a cross-sectional view of the electrophysiology catheter of FIG. 1 taken along line B-B.

FIG. 8 depicts the deflection of the neck region of the electrophysiology catheter of FIG. 1.

FIG. 9 depicts one configuration for varying the radius of curvature of the loop of the distal region of the catheter of FIG. 1.

DETAILED DESCRIPTION OF THE INVENTION

Figure 4:
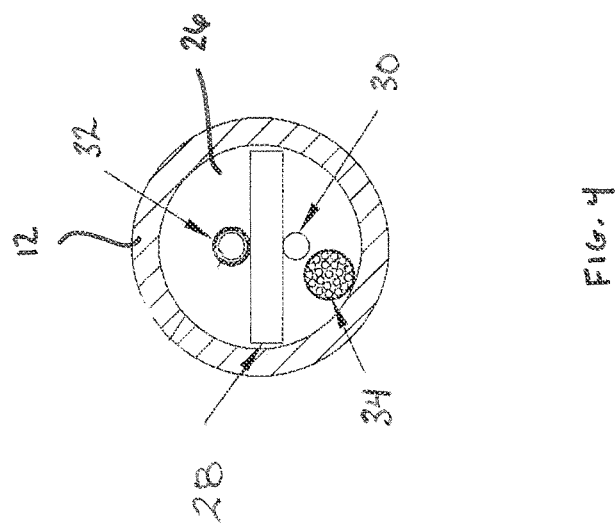
FIG. 4 is a cross-sectional view of the electrophysiology catheter of FIG. 1 taken along line A-A.

The present invention will be described with reference to an electrophysiology catheter utilized in cardiac electrophysiology studies, such as the Livewire Spiral HP™ and Inquiry™ Optima™ PLUS catheters of St. Jude Medical, Inc. It should be understood, however, that the present teachings may be applied to good advantage in other contexts as well.

Referring now to the figures, FIG. 1 depicts an electrophysiology ("EP") catheter 10 according to a first aspect of the present invention.

EP catheter 10 generally includes an elongate catheter body 12, which, in some embodiments, is tubular (e.g., it defines at least one lumen therethrough). Catheter body 12 includes a proximal region 14, a distal region 16, and a neck region 18 between proximal region 14 and distal region 16. One of ordinary skill in the art will appreciate that the relative lengths of proximal region 14, distal region 16, and neck region 18 depicted in FIG. 1 are merely illustrative and may vary without departing from the spirit and scope of the present invention. Of course, the overall length of catheter body 12 should be long enough to reach the intended destination within the patient's body.

Catheter body 12 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, may be utilized. Additional suitable materials for catheter body 12 include, without limitation, polyamide-based thermoplastic elastomers (namely poly(ether-block-amide), such as PEBAX®), polyester-based thermoplastic elastomers (e.g., HYTREL®), thermoplastic polyurethanes (e.g., PELLETHANE®, ESTANE®), ionic thermoplastic elastomers, functionalized thermoplastic olefins, and any combinations thereof. In general, suitable materials for catheter body 12 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 12 may vary along its length. In general, the basic construction of catheter body 12 will be familiar to those of ordinary skill in the art, and thus will not be discussed in further detail herein.

As seen in FIGS. 2A, 2B, 3A, and 3B, distal region 16 of catheter body 12 is predisposed into at least a partial loop. As one of ordinary skill in the art will appreciate, this loop shape allows distal region 16 to conform to the shape, for example, of a pulmonary vein ostium. One of ordinary skill in the art will also appreciate that the partial loop may take a number of configurations, depending on the intended or desired use of EP catheter 10, consistent with the present teachings. Therefore, it should be understood that the circular and elliptical loop configurations depicted in FIGS. 2B and 3B, respectively, are merely illustrative.

FIGS. 2A, 2B, 3A, and 3B also illustrate that distal region 16 includes a plurality of electrodes 20 disposed thereon. One of ordinary skill in the art will appreciate that electrodes 20 may be ring electrodes or any other electrodes suitable for a particular application of EP catheter 10. For example, where EP catheter 10 is intended for use in a contactless electrophysiology study, electrodes 20 may be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 20 may be employed for therapeutic purposes (e.g., cardiac ablation and/or pacing).

Referring again to FIG. 1, a handle 22 is coupled to proximal region 14 of catheter body 12. Handle 22 includes suitable actuators (e.g., knob 24) to control the deflection of catheter body 12 described in further detail below. Various handles and their associated actuators for use in connection with electrophysiology catheters are known, and thus handle 22 will not be described in further detail herein.

FIG. 4 is a cross-section of catheter body 12 taken along line A-A in FIG. 1 (e.g., within proximal region 14). An interior lumen 26 of catheter body 12 is visible. Also visible is a first deflection wire 28, a first activation wire 30, a second activation wire 32 (discussed in further detail below), and a collection of conductor wires 34 for conducting power and/or signals to and/or from electrodes 20.

First deflection wire 28 extends through at least a portion of proximal region 14 of catheter body 12. Preferably, first deflection wire 28 includes a first flattened section, as this configuration promotes deflection along a first axis while inhibiting deflection along other axes. One suitable material for first deflection wire 28 is stainless steel, though other materials can be employed without departing from the spirit and scope of the present invention.

First activation wire 30 extends from handle 22, where it is coupled to a suitable actuator, and is joined to the first flattened section of first deflection wire 28, for example by soldering. As such, forces acting on first activation wire 30, for example tension resulting from practitioner acting on a suitable actuator provided on handle 22, are transmitted to first deflection wire 28, thereby deflecting proximal region 14 of catheter body 12. Deflection of proximal region 14 is shown in FIGS. 5 and 6. For example, FIG. 6 shows proximal region 14 deflecting from a generally straight configuration (shown in phantom) in the direction of arrow 36 to a curve of approximately 180 degrees (shown in solid lines).

FIG. 7 is a cross-section of catheter body 12 taken along line B-B in FIG. 1 (e.g., within neck region 18). Visible in FIG. 7 are a second deflection wire 38, second activation wire 32, and conductors 34.

Second deflection wire 38 extends through neck region 18, and, in some embodiments of the invention, through at least a portion of distal region 16. Second deflection wire 38 also includes a second flattened section within neck region 18. Preferably, second deflection wire 38 is made of a shape memory material such as nickel titanium (e.g., Nitinol).

Second activation wire 32 extends from handle 22, where it is coupled to a suitable actuator, and is joined to the second flattened section of second deflection wire 38, for example by soldering. As such, forces acting on second activation wire 32, for example tension resulting from practitioner acting on a suitable actuator provided on handle 22, are transmitted to second deflection wire 38, thereby deflecting neck region 18 of catheter body 12. Deflection of neck region 18 is shown in FIGS. 6 and 8. For example, FIG. 8 shows, in phantom, neck region 18 deflected such that distal region 16 is no longer perpendicular to the remainder of catheter body 12 (e.g., deflection in the direction of arrow 40 shown in FIG. 6). This additional deflection advantageously allows a practitioner to "fine tune" the orientation of the loop of distal region 16. That is, by not limiting the plane of the loop of distal region 16 to being orthogonal to the longitudinal axis of catheter body 12, a practitioner can tailor the shape of EP catheter 10 to a particular patient's individual anatomy, thereby facilitating electrophysiology procedures.

At least a portion of second activation wire 32 may be surrounded by a spring coil 42. Spring coil 42 stabilizes neck region 18 when second deflection wire 38 is activated by second activation wire 32. The inner diameter of spring coil 42 is preferably slightly larger than the diameter of second activation wire 32.

As described above, in some embodiments of the invention, second deflection wire 32 extends distally into distal region 16. In these embodiments of the invention, the shape memory material of second deflection wire 32 may also serve to predispose distal region 16 into the looped configuration. That is, it is contemplated that second deflection wire 32 may also serve as a shaping wire for distal region 16. Optionally, the portion of second deflection wire 32 that extends into distal region 16 may be of a different cross-sectional configuration than the portion of second deflection wire extending through neck region 18. For example, the more distal portion of second deflection wire 32 may have a cylindrical cross-section, as opposed to the flat cross-section of the more proximal portion thereof.

It is also contemplated that the radius of curvature of the loop of distal region 16 may be adjustable, for example to conform to the varying sizes of pulmonary vein ostia of patients of different ages. This additional control may be provided, for example, by providing a third activation wire, such as wire 44, adapted to alter the radius of curvature of the loop of distal region 16. In some embodiments of the invention, one end (e.g., the distal end) of third activation wire 44 may be coupled to the tip of catheter body 12 (e.g., coupled to a tip electrode 46), while the other end (e.g., the proximal end) of third activation wire 44 may be coupled to a suitable actuator on handle 22. For example, FIG. 9 illustrates a configuration where pulling on activation wire 44 will cause distal region 16 to bend into or out of the plane of the page, thereby altering the radius of curvature of the loop of distal region 16.

Alternatively, in embodiments of the invention where second deflection wire 32 extends distally into distal region 16, second deflection wire 32 may itself serve as the activation wire that alters the radius of curvature of the loop. Still another mechanism for varying the radius of curvature of the loop of distal region 16 is described in U.S. application Ser. No. 12/004,643, filed 21 Dec. 2007, and hereby incorporated by reference as though fully set forth herein.

In use, EP catheter 10 is introduced into a patient's body proximate an area of interest, such as a pulmonary vein ostium. Of course, EP catheter may be introduced surgically (e.g., via an incision in the patient's chest) or non-surgically (e.g., navigated through the patient's vasculature to a desired site). First deflection wire 28 may be actuated in order to deflect proximal region 14 of catheter body 12 such that distal region 16 is oriented generally towards the ostium of interest. Thereafter, second deflection wire 38 may be actuated to deflect neck region 18 of catheter body 12 in order to "fine tune" the position of distal region 16 relative to the ostium of interest. Where such additional refinement is desirable, the radius of curvature of the loop of distal region 16 may also be adjusted. Electrodes 20 may then be employed for diagnostic or therapeutic purposes.

Although several embodiments of this invention have been described above with a certain degree of particularity, those skilled in the art could make numerous alterations to the disclosed embodiments without departing from the spirit or scope of this invention. For example, though FIG. 6 depicts proximal region 14 and neck region 18 of catheter body 12 deflecting in the same plane, the deflection mechanisms (e.g., first deflection wire 28/first activation wire 30 and second deflection wire 38/second activation wire 32) may instead be oriented such that proximal region 14 and neck region 18 of catheter body 12 depict in different planes. As another example, though FIG. 6 depicts only unidirectional deflection, either or both of proximal region 14 and neck region 18 may be configured for bidirectional deflection in a single plane and/or unidirectional or bidirectional deflection in multiple planes.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrophysiology catheter comprising:
   a tubular catheter body having a proximal region, a neck region, and a distal region predisposed into at least a partial loop disposed in a plane;
   at least one electrode disposed on the distal region;
   a handle joined to the proximal region;
   a first deflection mechanism extending from the handle through at least a portion of the proximal region of the catheter body to facilitate deflection of the proximal region of the tubular catheter body such that the at least a partial loop of the distal region deflects from the plane; and
   a second deflection mechanism extending from the handle through the neck region and at least a portion of the distal region to deflect the neck region of the tubular catheter body such that the at least a partial loop of the distal region deflects from the plane.

2. The electrophysiology catheter of claim 1, wherein at least a portion of the first deflection mechanism comprises a first flattened section extending through at least a portion of the proximal region of the catheter body.

3. The electrophysiology catheter of claim 2, wherein the first deflection mechanism comprises a first activation wire extending from the handle and joined to the first flattened section.

4. The electrophysiology catheter of claim 1, wherein at least a portion of the second deflection mechanism comprises a second flattened section extending through the neck region and at least a portion of the distal region.

5. The electrophysiology catheter of claim 4, wherein the second deflection mechanism comprises a second activation wire extending from the handle and joined to the second flattened section.

6. The electrophysiology catheter of claim 1, further comprising means for altering a radius of curvature of the at least a partial loop.

7. An electrophysiology catheter comprising:
   a tubular catheter body having a proximal region, a neck region, and a distal region predisposed into at least a partial loop disposed in a plane;
   at least one electrode disposed on the distal region;
   a first deflection assembly operable to deflect the proximal region of the tubular catheter body such that the at least a partial loop of the distal region deflects from the plane;
   a second deflection assembly operable to deflect the neck region of the tubular catheter body such that the at least a partial loop of the distal region deflects from the plane; and
   a handle joined to the proximal region, the handle comprising:
      a first actuator operably coupled to the first deflection assembly; and
      a second actuator operably coupled to the second deflection assembly.

8. The electrophysiology catheter of claim 7, wherein the first deflection assembly comprises a first deflection wire, and wherein the first deflection wire comprises a first flattened section extending through at least a portion of the proximal region of the catheter body.

9. The electrophysiology catheter of claim 8, wherein the first deflection assembly further comprises a first activation wire extending from the handle and joined to the first flattened section of the first deflection wire.

10. The electrophysiology catheter of claim 7, wherein the second deflection assembly comprises a second deflection wire, and wherein the second deflection wire comprises a second flattened section extending through the neck region and at least a portion of the distal region.

11. The electrophysiology catheter of claim 10, wherein the second deflection assembly further comprises a second activation wire extending from the handle and joined to the second flattened section of the second deflection wire.

12. The electrophysiology catheter of claim 7, further comprising means for altering a radius of curvature of the at least a partial loop.

13. The electrophysiology catheter of claim 7, wherein the at least a partial loop of the distal region comprises an active region.

14. The electrophysiology catheter of claim 13, wherein the active region comprises a plurality of electrodes.

15. An electrophysiology catheter comprising:
   a tubular catheter body having a proximal region, a neck region, and a distal region predisposed into at least a partial loop disposed in a plane;
   at least one electrically-active region disposed on the distal region;
   a handle joined to the proximal region, the handle comprising a first actuator and a second actuator;
   a first deflection mechanism comprising a first deflection wire operably coupled to the first actuator such that actuation of the first actuator causes deflection in the proximal region that causes the at least a partial loop of the distal region to deflect from the plane; and
   a second deflection mechanism comprising a second deflection wire operably coupled to the second actuator such that actuation of the second actuator causes deflection in the neck region that causes the at least a partial loop of the distal region to deflect from the plane.

16. The electrophysiology catheter of claim 15, wherein at least a portion of the first deflection mechanism comprises a first flattened section extending through at least a portion of the proximal region of the catheter body.

17. The electrophysiology catheter of claim 16, wherein the first deflection mechanism comprises a first activation wire extending from the handle and joined to the first flattened section.

18. The electrophysiology catheter of claim 15, wherein at least a portion of the second deflection mechanism comprises a second flattened section extending through the neck region and at least a portion of the distal region.

19. The electrophysiology catheter of claim 18, wherein the second deflection mechanism comprises a second activation wire extending from the handle and joined to the second flattened section.

20. The electrophysiology catheter of claim 15, further comprising means for altering a radius of curvature of the at least a partial loop.

* * * * *